(12) United States Patent
Dayhoff et al.

(10) Patent No.: US 7,611,477 B2
(45) Date of Patent: Nov. 3, 2009

(54) TOE LIFT STRAP

(75) Inventors: William Alfred Dayhoff, Milburn, OK (US); Thecia Venita Dayhoff, Milburn, OK (US)

(73) Assignees: William A. Dayhoff, Milburn, OK (US); Thecia V. Dayhoff, Milburn, OK (US)

( * ) Notice: Subject to any disclaimer, the term of this patent is extended or adjusted under 35 U.S.C. 154(b) by 0 days.

(21) Appl. No.: 11/825,964

(22) Filed: Jul. 11, 2007

(65) Prior Publication Data

US 2009/0018478 A1   Jan. 15, 2009

(51) Int. Cl.
    A61F 5/00 (2006.01)
(52) U.S. Cl. .......................... 602/29; 602/27
(58) Field of Classification Search ............ 602/27–29, 602/23; D24/192, 190
    See application file for complete search history.

(56) References Cited

U.S. PATENT DOCUMENTS

| | | | |
|---|---|---|---|
| 1,402,282 A | 1/1922 | Chevrier | |
| 2,525,237 A | 10/1950 | Park | |
| 2,584,010 A * | 1/1952 | Goffredo | .................... 602/28 |
| 2,847,997 A | 8/1958 | Andrews | |
| 3,504,668 A | 4/1970 | Boudon | |
| 3,976,059 A | 8/1976 | Lonordo | |
| 3,986,501 A | 10/1976 | Schad | |
| 4,289,122 A | 9/1981 | Mason | |
| 4,371,161 A | 2/1983 | Williams | |
| 4,955,370 A | 9/1990 | Pettine | |
| 5,088,479 A | 2/1992 | DeToro | |
| 5,090,138 A | 2/1992 | Borden | |
| 5,219,324 A | 6/1993 | Hall | |
| 5,277,699 A | 1/1994 | Williamson | |
| 5,291,904 A | 3/1994 | Walker | |
| 5,370,604 A | 12/1994 | Bernardoni | |
| 5,382,224 A | 1/1995 | Spangler | |
| 5,486,157 A | 1/1996 | DiBenedetto | |
| 5,676,641 A * | 10/1997 | Arensdorf et al. | ............. 602/27 |
| 5,697,893 A | 12/1997 | Rhenter | |
| 5,776,090 A | 7/1998 | Bergmann | |
| 5,897,515 A | 4/1999 | Wilner et al. | |
| 6,270,468 B1 | 8/2001 | Townsend et al. | |
| 6,299,587 B1 | 10/2001 | Birmingham | |
| 6,302,858 B1 | 10/2001 | DeToro et al. | |
| 6,409,692 B1 | 6/2002 | Covey | |
| 6,409,695 B1 | 6/2002 | Connelly | |
| 6,676,618 B2 | 1/2004 | Anderson | |

(Continued)

OTHER PUBLICATIONS

Patent Application #2002/0129821, Sep. 19, 2002, Trieloff Figure 2, Item 20, 22, 40, Background of Inv., Line 3 "foot drop".

Primary Examiner—Kim M Lewis

(57) ABSTRACT

The Toe Lift Strap is a foot support system primarily for stroke victims that do not have muscular control of their foot. This loss of muscular control allows the foot to turn under and they cannot raise their toe. It comprises of a strap that is attached to the user just below the knee. This strap has a small loop to which a 6" wide therapeutic rubber band is attached. The other end of the 6" wide therapeutic rubber band is attached to the lower lace area or lower strap of a shoe worn by the user. It provides for support of the toe and rotation of the foot so that the user can walk with the foot in a normal position for walking.

4 Claims, 6 Drawing Sheets

U.S. PATENT DOCUMENTS

| | | |
|---|---|---|
| 6,726,645 B1 | 4/2004 | Davis |
| 6,827,696 B1 | 12/2004 | Maguire |
| 6,860,864 B2 | 3/2005 | Meyer |
| 6,926,687 B2 | 8/2005 | Shields |
| 7,094,213 B1 | 8/2006 | Cook |
| 7,112,181 B1 | 9/2006 | DeToro et al. |
| 7,112,182 B1 * | 9/2006 | Zahiri .................. 602/27 |
| 7,354,413 B2 * | 4/2008 | Fisher .................. 602/29 |
| 7,458,950 B1 * | 12/2008 | Ivany .................. 602/28 |

* cited by examiner

| ITEM | DESCRIPTION |
|---|---|
| #1 | BELT |
| #2 | LOOP ATTACHED TO BELT |
| #3 | DOUBLE D-RING BUCKLE |
| #4 | 6" X 30" THERAPEUTIC RUBBER BAND |

TOE LIFT STRAP

FIELD OF THE INVENTION

This invention relates to an embodiment that is attached to the user's calf and shoe, that will assist the user to position the foot flat to the floor, assist in holding the toe up, and position the foot in the proper position for normal walking.

BACKGROUND

Drop foot is characterized by insufficient control of the muscles that hold the foot and ankle in position for normal walking. The toes cannot be held up because of the loss of muscular control. The foot may turn under while walking so that the victim walks on the side of their foot. It may also be turned inward or outward so that while walking, the toe drags and further twists the foot and make walking very difficult, and could result in serious injury to the victim. These symptoms are typical of a person that has suffered a stroke.

Drop foot suffers would benefit greatly by having a device that would help hold the foot in a normal position while undergoing therapy to begin the process of walking again. If the foot can be held in a normal position, and has flexibility to allow the foot to move properly, the control of the muscles can be regained, and can be strengthened in the therapeutic process. Repeated normal movement is very important to a stroke victim's recovery and use of the foot.

My review of patents reveled there have been numerous attempts in make a device that would support the foot when a victim loses muscular control of the foot and ankle. I have chosen three (3) such patents that very use some of the same ideas utilized in our patent.

The first is Thompson's U.S. Pat. No. 5,860,423; the very nature of the length of the description illustrates the complication that is associated with the invention. While it does use elastic material to raise the toe of the shoe, it is limited in the flex that can be provided. It also involves permanent installation of several items, directly to the shoe. The elastic straps are attached to the shoe at a point that would require a stronger elastic band than would be required if the attachment point was closer to the toe of the shoe. It would have very little effect on preventing the foot from turning onto a side of the foot that is almost always present with stroke victims.

The second is Shield's U.S. Pat. No. 6,926,687: Shield uses straps to make to lift mechanism work. It would not provide any means to help with the turning under of the foot of a stroke victim. Also the steel shanks that insert into the heel area of the shoe, could be uncomfortable.

The third is Trieloff's Patent Application #2002/0129821 A1; Trieloff uses some of the same basic applications methods that we have used in our invention. However, Trieloff's device is very limited in use and application. The portion that fits onto the foot would limit what could be done to lift the foot. It certainly would be difficult to wear Trieloff's device with a shoe. It would not provide any means of rotating the foot to prevent a stroke patient from walking on the side of their foot.

BRIEF DESCRIPTION OF DRAWINGS

FIG. #1: This is an illustration of the basic invention. It consists of a belt made of 1" wide material that is soft and with minimum stretch. The belt has a buckle made with two (2) D-rings and they are secured with a small loop. The small loop is closed and secured with two (2) rivets. Approximately three (3) inches from the belt buckle, a loop is also attached to the above belt. The loop is secured with one (1) rivet. The second part is a 6" wide by 32" long therapeutic rubber band.

FIG. #2: This illustrates a view of the outside of the right leg with the invention installed on a typical user. The knee belt is secured below the knee, one (1) end of the 6" wide therapeutic rubber band tied to the shoe lace, at the toe, (not visible in this illustration, see FIGS. #3 and #4), it is then taken under the shoe and the other end tied to the loop that is secured to the knee belt. The 6"0 wide therapeutic rubber band is spread evenly on the outside of the right foot in a position that would provide for good toe lift and rotation of the foot so that the foot would set flat to the floor. The shoe is a typical walking shoe.

Figure 1:
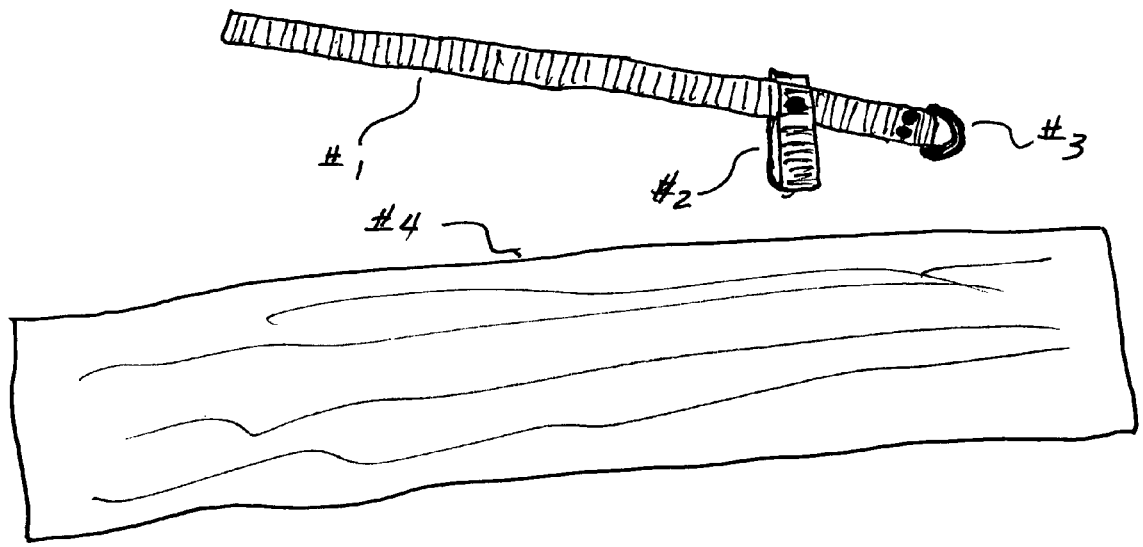
Figure 2:
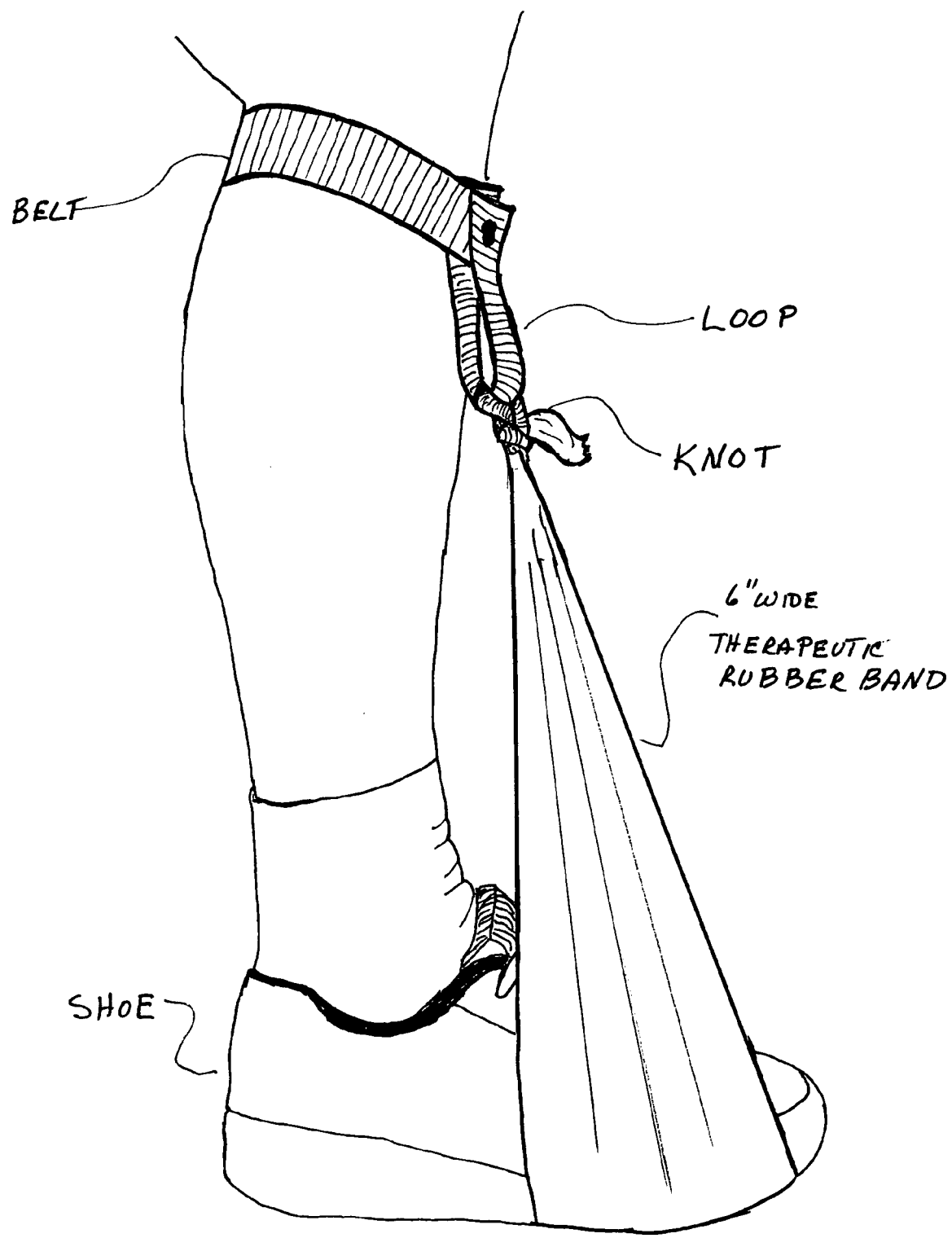
Figure 3:
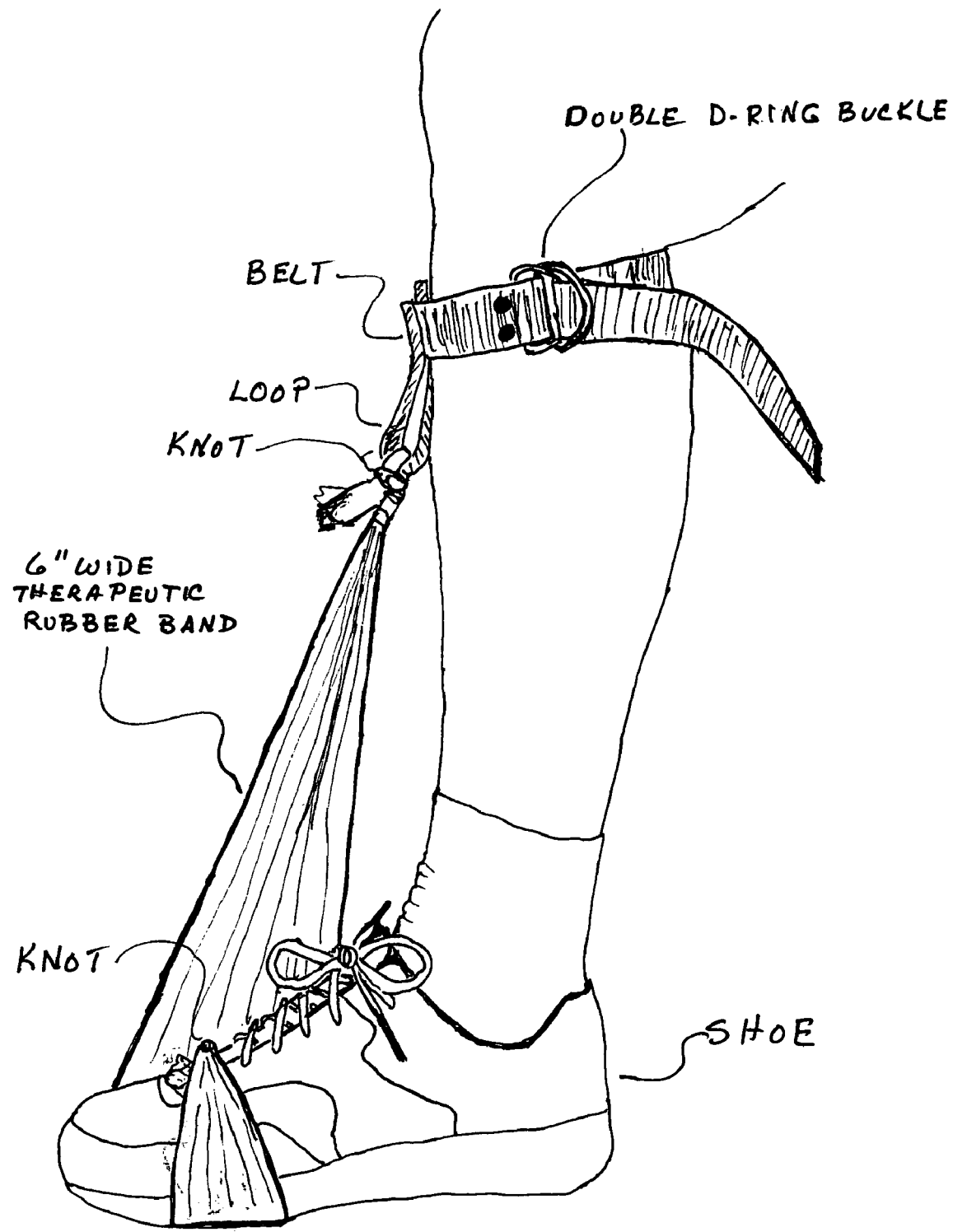
Figure 4:
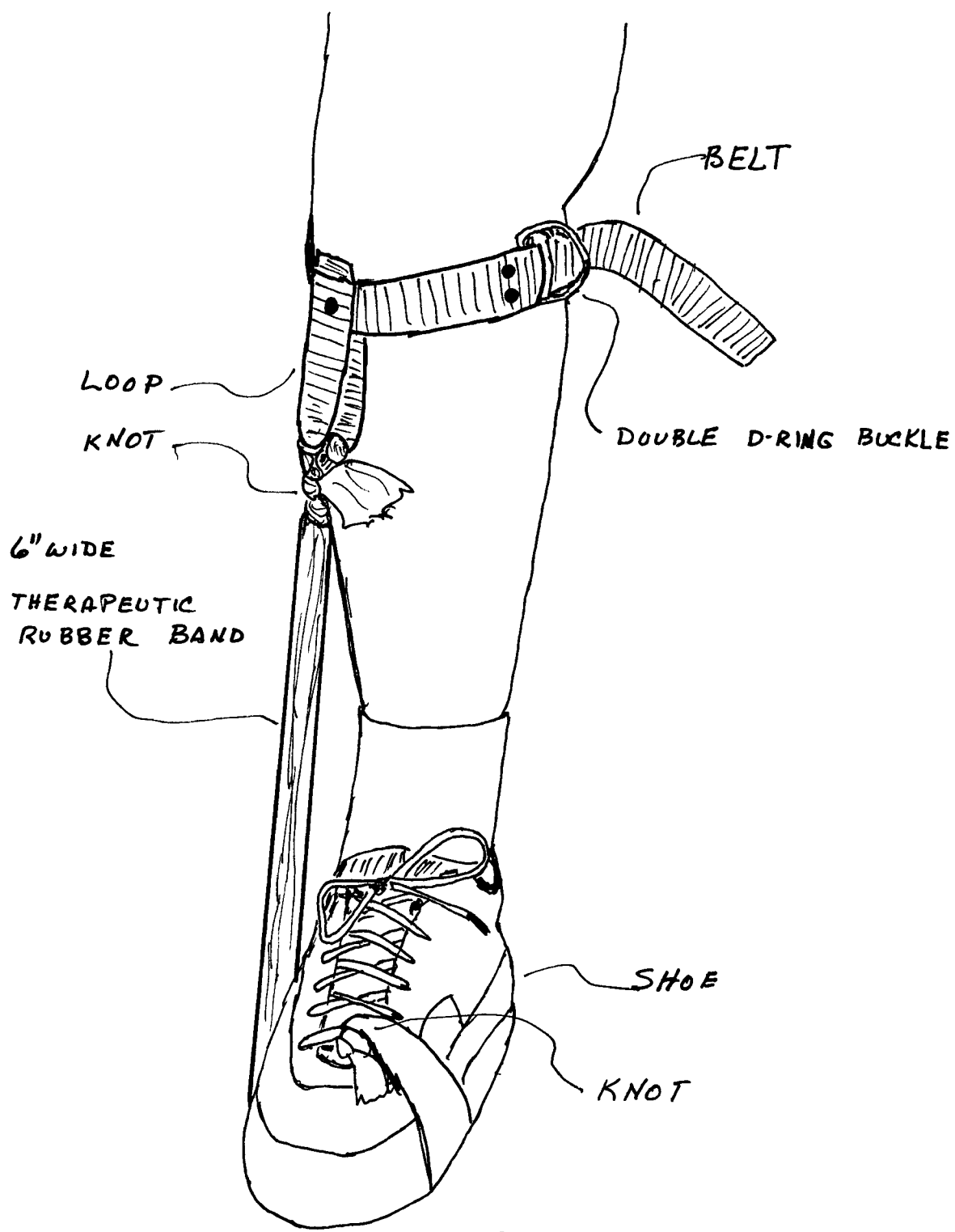
Figure 5:
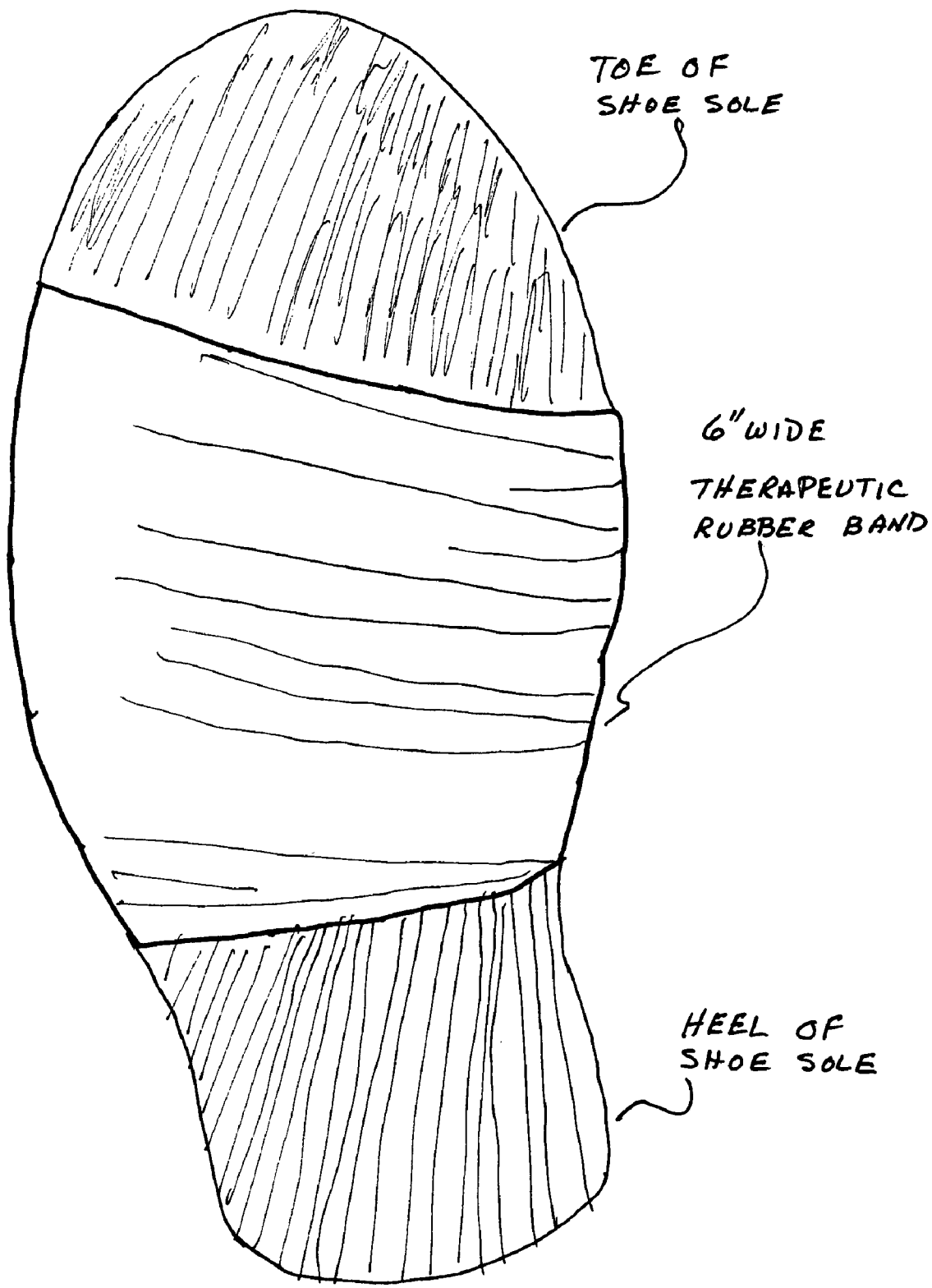
Figure 6:
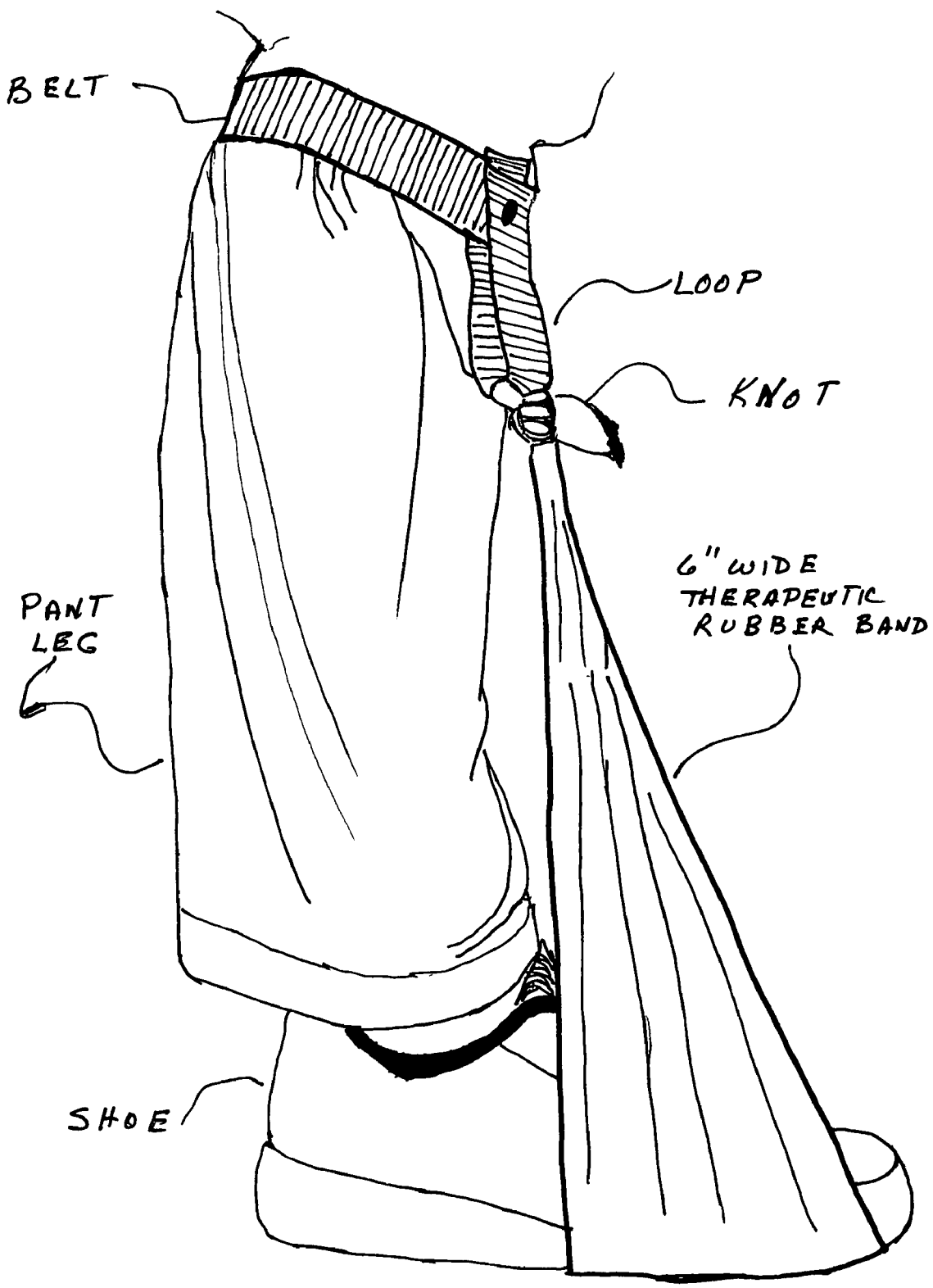

FIG. #3: This illustrates a view of the inside of the right leg with the invention installed on a typical user. The knee belt is secured below the knee, one (1) end of the 6" wide therapeutic rubber band tied to the shoe lace, at the toe, it is then taken under the shoe and the other end tied to the loop that is secured to the knee belt. The 6" wide therapeutic rubber band is spread evenly on the inside of the right foot in a position that would provide for good toe lift and rotation of the foot so that the foot would set flat to the floor. The shoe is a typical walking shoe.

FIG. #4: This illustrates a front view of the right leg. This gives a good view of how the 6" wide therapeutic rubber band is tied to the lace at the toe of the shoe, and is then wrapped under the shoe and stretched to the proper tension and tied to the loop on the knee belt. This illustration shows how the invention produces a torque force to pull the inside of the foot down, the outside of the foot up, and raising the toe.

FIG. #5: This is an illustration of the 6" wide therapeutic rubber band as it goes under the shoe. The view is with the toe closer to the viewer and the heel further away.

FIG. #6: This is the same as FIG. #2, except here the user is wearing a pair of long pants.

DESCRIPTION OF THE INVENTION

The "Toe Lift Strap" is an embodiment that consists of three (3) major parts. The first part is the strap that is attached to the user as a belt. This belt is to be made of material that is soft and comfortable for the user. It should be approximately 1" wide and sufficiently long to go around the user's leg just below the knee. The strap is held in place by the use of a Double D-ring buckle. The Double D-ring buckle allows for infinite adjustment to obtain the proper fit of the user. The Double D-ring buckle and be attached to the belt using rivets or can be stitching on using heavy thread.

The second part of this embodiment is attached to the above described belt; is a loop that can be made of the same material as the belt, and is held to the belt by sewing with heavy thread of rivet.

The third and final part is a 6" wide therapeutic rubber band that is approximately 32" in length.

Proper fitting of the embodiment is as follows:
1. Fit the 1" belt around the leg of the user, above the calf and just below the knee.
2. Tighten the belt for a firm fit, but allow enough space between the belt and the user so that a finger can be inserted between the leg of the user and the strap.
3. Using the 6" inch therapeutic rubber band, tie one end to the lowest shoe lace or strap of the user's shoe.
4. If the user has a tendency to walk on the outside of the foot, wrap the 6" therapeutic band around the shoe by going to the inside part of the foot and under the shoe at the ball of the foot. Extend the free end up to the already installed belt and through the loop attached to the strap. Pull the 6" therapeutic rubber band through the loop and then pull enough to position the foot so that it will sit flat with respect to the floor. When the proper tension is obtained, tie the free end of the 6" therapeutic rubber band, around the tense portion of the band, using two (2) half-hitches very close to the loop end.
5. If more lift of the toe is desired, slide the 6" wide therapeutic rubber band forward on the foot.
6. To align the foot so that the toes are straight forward, using the belt, adjust the position of the loop, on the knee belt, to the desired location. If the toes are pointed in, adjust the point of tension of the loop to the outside of the leg. If the toes are pointed out, adjust the point of tension of the loop to the inside of the leg.
7. Therapeutic rubber bands come in various strengths; thin, medium, heavy and extra heavy. If the desired lift is not obtained with a medium band, increase the lift by using stronger band. If less tension is required, reduce the tension by using a lighter strength band.

The invention claimed is:

1. A method for positioning the foot, comprising the steps of:
   providing a foot device consisting of a knee belt adapted to be secured on a user below the knee on a leg, the knee belt comprising a double D-ring buckle at one end thereof for adjusting the fit of the belt to the user's leg; a loop firmly attached to the knee belt at approximately 3 inches from the double D-ring buckle end of the belt, wherein the loop is attached to the belt via a rivet or stitching; a 6 inch wide therapeutic rubber band having a length of approximately 32 inches and first and second ends;
   placing the knee belt on the user below the knee;
   tightening the belt for a firm fit;
   attaching a first end of the therapeutic rubber band to a shoe adjacent the toes;
   wrapping the band under the shoe from the inside of the shoe around to the outside of the shoe such that the band is evenly spread on the outside of the shoe in a position that provides good toe lift and rotations of the foot such that the foot will sit flat on the floor; and
   extending the second end of the band to the loop and attaching it thereto.

2. The method of claim 1, wherein the device is adapted to be worn on either the left or right leg.

3. The method of claim 1, wherein the therapeutic band is slid forward on the foot to achieve greater toe lift.

4. The method of claim 1, wherein the band can be changed to thin, medium, heavy and extra heavy in order to increase or decrease the strength of the band to provide the correct amount of toe lift.

* * * * *